US012678490B2

(12) United States Patent
Beals et al.

(10) Patent No.: US 12,678,490 B2
(45) Date of Patent: *Jul. 14, 2026

(54) PHARMACEUTICAL COMBINATIONS COMPRISING INSULIN AND AT LEAST AN AGENT SELECTED FROM MELOXICAM, BROMFENAC SODIUM, ACETYLSALICYLIC ACID, SALICYCLIC ACID AND PARACETAMOL

(71) Applicant: Eli Lilly and Company, Indianapolis, IN (US)

(72) Inventors: John Michael Beals, Indianapolis, IN (US); Eric Dwayne Hawkins, Carmel, IN (US); Anthony Shane Ransdell, Plainfield, IN (US); Shantanu Virendra Sule, Arlington, MA (US); Monica Rixman Swinney, Stoneham, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 1121 days.

This patent is subject to a terminal disclaimer.

(21) Appl. No.: 17/551,904

(22) Filed: Dec. 15, 2021

(65) Prior Publication Data

US 2022/0175891 A1      Jun. 9, 2022

Related U.S. Application Data

(62) Division of application No. 16/645,199, filed as application No. PCT/US2018/048667 on Aug. 3, 2018, now Pat. No. 11,510,967.

(60) Provisional application No. 62/555,974, filed on Sep. 8, 2017.

(51) Int. Cl.
| | |
|---|---|
| A61K 38/28 | (2006.01) |
| A61K 31/167 | (2006.01) |
| A61K 31/196 | (2006.01) |
| A61K 31/5415 | (2006.01) |
| A61K 31/573 | (2006.01) |
| A61K 31/625 | (2006.01) |
| A61K 31/727 | (2006.01) |
| A61K 33/30 | (2006.01) |
| A61K 47/10 | (2017.01) |
| A61P 3/10 | (2006.01) |

(52) U.S. Cl.
CPC ............ *A61K 38/28* (2013.01); *A61K 31/167* (2013.01); *A61K 31/196* (2013.01); *A61K 31/5415* (2013.01); *A61K 31/573* (2013.01);

*A61K 31/625* (2013.01); *A61K 31/727* (2013.01); *A61K 33/30* (2013.01); *A61K 47/10* (2013.01); *A61P 3/10* (2018.01)

(58) Field of Classification Search
CPC .... A61K 38/28; A61K 31/167; A61K 31/196; A61K 31/5415; A61K 31/573; A61K 31/625; A61K 31/727; A61K 31/60; A61P 3/10
See application file for complete search history.

(56) References Cited

U.S. PATENT DOCUMENTS

| | | | |
|---|---|---|---|
| 2015/0112302 A1* | 4/2015 | Chattaraj | ................ A61P 43/00 604/257 |
| 2017/0056478 A1 | 3/2017 | Akers et al. | |

FOREIGN PATENT DOCUMENTS

| | | | | |
|---|---|---|---|---|
| CN | 101735048 | 6/2010 | | |
| WO | 02085376 | 10/2002 | | |
| WO | 2012174478 | 12/2012 | | |
| WO | 2015106269 | 7/2015 | | |
| WO | WO-2017072415 A1 * | 5/2017 | .............. | A61P 29/00 |

OTHER PUBLICATIONS

M. Distel, Safety of Meloxicam: a Global Analysis of Clinical Trials, British Journal of Rheumatology 1996;35(snppL I):68-77.*
Eli Lilly, PRoduct Monograph, Humalog, published online 2017.*
Fda, Drug Label, Humalog® Insulin Lispro Injection (rDNA Origin) Description, pp. 1-12, published online 2010. (Year: 2010).*
Hansen, D. G., Aures, D., & Grossman, M. I. (1978). Histamine augments gastric ulceration produced by intravenous aspirin in cats. *Gastroenterology*, 74(3), 540-543.
International Search Report of the International Searching Authority pertaining to International Application No. PCT/US2018/048667; Date of Mailing: Jan. 23, 2019; 8 pages.
Written Opinion of the International Searching Authority pertaining to International Application No. PCT/US2018/048667; Date of Mailing: Jan. 23, 2019; 14 pages.

* cited by examiner

*Primary Examiner* — Erinne R Dabkowski
(74) *Attorney, Agent, or Firm* — Megan Fuller

(57) ABSTRACT

The present invention relates to pharmaceutical insulin compositions comprising insulin, a preservative, and at least one selected from the group consisting of aspirin, acetaminophen, dexamethasone, heparin, meloxicam, bromfenac sodium, salicylic acid; and the use of the compositions to treat diabetes.

1 Claim, No Drawings

PHARMACEUTICAL COMBINATIONS COMPRISING INSULIN AND AT LEAST AN AGENT SELECTED FROM MELOXICAM, BROMFENAC SODIUM, ACETYLSALICYLIC ACID, SALICYCLIC ACID AND PARACETAMOL

This application is a divisional application of U.S. application Ser. No. 16/645,199, filed on Mar. 6, 2020, which claims priority to a 371 national application No. PCT/US2018/48667, filed on Mar. 30, 2018, which claims priority to U.S. Provisional Application No. 62/555,974, filed on Sep. 8, 2017. The disclosure of each of the above applications is incorporated herein by reference in its entirety.

The present invention provides an insulin composition comprising insulin, preservative, and at least one agent selected from the group consisting of meloxicam, bromfenac sodium, acetylsalicylic acid, salicylic acid, paracetamol, heparin, and dexamethasone. The present insulin composition can extend the wear-time of a continuous subcutaneous insulin infusion (CSII) therapy device, by maintaining efficacy and stability.

Commercially available insulin infusion sets for CSII are currently indicated for 2-3 days use. Use of CSII at a single site is limited due to impaired infusion site efficacy after approximately 3 to 5 days. An infusion set that lasts greater than 3 days, and preferably 7 to 14 days, and in some embodiments, up to 21 days, is desired for patient convenience, consistent efficacy, to reduce waste, and to ultimately enable a once-weekly or once-biweekly change-over time frame.

Certain methods and systems for inhibiting foreign body responses in diabetic patients and to decrease infusion site loss are disclosed in WO 2015/061493 (Medtronic). Despite these efforts, there is a need for additional means to extend the efficiency of single site CSII for patients with diabetes.

The insulin composition of this invention is suited for use with a pump and an infusion set and offers patients desired enhanced usage time at a single site for CSII.

The present invention provides a composition comprising insulin, preservative, and at least one agent selected from the group consisting of meloxicam, bromfenac sodium, acetylsalicylic acid, paracetamol, salicylic acid, heparin, and dexamethasone.

In an embodiment the composition comprises insulin, preservative, and at least one agent selected from the group consisting of sodium, acetylsalicylic acid, paracetamol, and salicylic acid. In an embodiment is a composition comprising insulin, preservative, and at least one agent selected from the group consisting of meloxicam, bromfenac sodium, and dexamethasone.

In an embodiment the preservative is m-cresol. In certain embodiments the preservative is phenol. In certain embodiments, the preservative is phenol and m-cresol.

In addition, the present invention also provides a method of treating diabetes comprising administering to a human in need thereof an effective dose of a pharmaceutical composition comprising insulin, preservative, and at least one agent selected from the group consisting of meloxicam, bromfenac sodium, acetylsalicylic acid, paracetamol, salicylic acid, heparin, and dexamethasone.

In addition, the present invention provides a pharmaceutical composition for use in therapy. More particularly, the present invention provides a pharmaceutical composition for use in the treatment of diabetes. The present invention also provides the use of a pharmaceutical composition in the manufacture of a medicament for the treatment of diabetes wherein the pharmaceutical composition comprises insulin, preservative, and at least one agent selected from the group consisting of meloxicam, bromfenac sodium, acetylsalicylic acid, paracetamol, salicylic acid, heparin, and dexamethasone.

In addition, the present invention provides an article of manufacture comprising a pharmaceutical composition comprising insulin, preservative, and at least one agent selected from the group consisting of meloxicam, bromfenac sodium, acetylsalicylic acid, paracetamol, salicylic acid, heparin, and dexamethasone.

More particularly, in certain aspects, the article of manufacture is a multi-use vial, a cartridge, a re-usable pen injector, a pump device for continuous subcutaneous insulin infusion therapy, and an article for use in a pump device for continuous subcutaneous insulin infusion therapy.

In an embodiment, this invention provides a pharmaceutical composition comprising:
a. insulin;
b. zinc, in a total concentration from about 0.2 mM to about 4 mM;
c. a preservative;
d. a buffer; and
at least one agent selected from the group consisting of meloxicam, bromfenac sodium, acetylsalicylic acid, salicylic acid, and paracetamol.

In an embodiment, this invention provides a pharmaceutical composition comprising:
a. insulin;
b. zinc, in a total concentration from about 0.2 to about 4 mM;
c. a preservative;
d. a buffer; and
at least one agent selected from the group consisting of acetylsalicylic acid, salicylic acid, and paracetamol.

In an embodiment, a buffer is for example, at least one selected from the group consisting of citrate, phosphate and TRIS.

In an embodiment, the insulin component in the composition is an ultra rapid-acting insulin. In a further embodiment, the composition comprises m-cresol.

In an embodiment, this invention provides a pharmaceutical composition comprising: a rapid-acting insulin; zinc, in a concentration from about 0.2 mM to about 4 mM; a preservative; and
at least one agent selected from the group consisting of meloxicam, bromfenac sodium, acetylsalicylic acid, salicylic acid, and paracetamol.

In an embodiment, this invention provides a pharmaceutical composition comprising: a rapid-acting insulin; zinc, in a concentration from about 0.2 mM to about 4 mM; a preservative; and
at least one agent selected from the group consisting of meloxicam, bromfenac sodium, acetylsalicylic acid, salicylic acid, heparin, paracetamol, and dexmethasone.

In certain embodiments, the compositions of the present invention have concentrations of the insulin from about 40 to about 1000 IU/mL. In certain embodiments, the composition of the present invention have concentrations of the insulin from about 100 to about 500 IU/mL. In certain embodiments, the compositions of the present invention have concentrations of the insulin from about 100 to about 300 IU/mL. In certain preferred embodiments, the compositions comprise an insulin concentration of about 100 IU/mL or about 200 IU/mL.

When used herein, the term "composition" refers to a combination of insulin and the other ingredients or excipients wherein the insulin and other ingredients or excipients are in a single combined formulation, typically an aqueous formulation.

As used herein, the term "about" means within plus or minus 10 percent. The term may preferably mean within plus or minus 5 percent. In certain embodiments, the term may preferably mean within plus or minus 2 percent.

"Insulin" as used herein means human insulin or an insulin analog. Insulin analogs are well-known and include for example, but are not limited to, insulin lispro (commercially available as HUMALOG®), insulin aspart (commercially available as NOVOLOG®), insulin glulisine (commercially available as APIDRA®). In one preferred embodiment, insulin is insulin lispro. In one preferred embodiment, insulin is ultra-rapid-acting insulin. In one preferred embodiment, the insulin is a rapid-acting insulin.

As used herein, "rapid-acting insulin" means an insulin that acts quickly to minimize the rise in blood sugar that typically follows eating. For example, this type of insulin typically begins to work in about 15 minutes after injection or dosage, peaks in about one hour, and continues to work for about 2 to 4 hours after dosage. The skilled artisan readily recognizes that rapid-acting insulins include, for example, insulin lispro and other commercially available insulins.

As used herein, "ultra-rapid-acting insulin" means an insulin that begins to work about 25% to about 50% faster than a "rapid-acting" insulin. For example, an ultra-rapid insulin may begin to work within about 5 to about 10 minutes after dosage. The artisan will recognize that ultra-rapid-acting insulins may include for example, FIASP® and other ultra-rapid-acting insulin formulations.

Meloxicam, bromfenac sodium, acetylsalicylic acid, paracetamol, salicylic acid, heparin, and dexamethasone are well-known agents. As used herein, "meloxicam" means IUPAC: 4-hydroxy-2-methyl-N-(5-methyl-2-thiazolyl)-2H-1,2-benzothiazine-3-carboxamide 1,1-dioxide. As used herein, "bromfenac sodium" means IUPAC: Sodium 2-[2-amino-3-(4-bromobenzoyl)phenyl]acetate.

As used herein, "acetylsalicylic acid" means IUPAC: 2-acetoxybenzoic acid, also known as aspirin or acetylsalicylate. As used herein "paracetamol" means IUPAC: N-(4-hydroxypehnyl)acetamide, also known as 4-acetamidophenol or acetaminophen. "Salicylic acid" as used herein means IUPAC: 2-hydroxybenzoic acid, a known hydrolysis product of aspirin. As used herein "heparin" means IUPAC Name: (2R,3R,4R,5S,6S)-6-[(2R,3R,4R,5R,6S)-6-[(2S,3S,4S,5R,6R)-6-[(2S,3S,4R,5R,6R)-5-acetamido-4,6-dihydroxy-2-(sulfooxymethyl)oxan-3-yl]oxy-2-carboxy-4-hydroxy-5-sulfooxyoxan-3-yl]oxy-2-(hydroxymethyl)-5-(sulfoamino)-4-sulfooxyoxan-3-yl]oxy-3,4-dihydroxy-5-sulfooxyoxane-2-carboxylic acid, also known as heparin sodium and heparin sulfate. As used herein "dexamethasone" means IUPAC Name: (8S,9R,10S,11S,13S,14S,16R,17R)-9-fluoro-11,17-dihydroxy-17-(2-hydroxyacetyl)-10,13,16-trimethyl-6,7,8,11,12,14,15,16-octahydrocyclopenta[a]phenanthren-3-one, also known as dexamethasone sodium phosphate. In one preferred embodiment, the composition includes paracetamol. In an embodiment the composition includes acetylsalicylic acid. In an embodiment, the composition includes heparin. In an embodiment, the composition includes dexamethasone. In an embodiment, the composition includes dexamethasone and salicylic acid. In an embodiment the agent is at least one selected from the group consisting of aspirin and heparin. In an embodiment the agent is at least one selected from the group consisting of salicylic acid and paracetamol. In an embodiment the agent is at least one selected from the group consisting of salicylic acid and acetylsalicylic acid. In an embodiment the agent is at least one selected from the group consisting of salicylic acid and heparin. In an embodiment the composition includes meloxicam. In an embodiment the composition includes bromfenac sodium. In an embodiment, the agent is at least one selected from the group consisting of acetylsalicylic acid, meloxicam, and bromfenac sodium.

In an embodiment, acetylsalicylic is present in an amount of from about 780 mg/mL to about 16,000 mg/mL. In an embodiment, acetylsalicylic acid is present in an amount of from about 0.18 mg/mL to about 1600 mg/mL. In an embodiment, acetylsalicylic acid is present at a concentration of about 10 mM. In an embodiment, acetylsalicylic acid is present at a concentration of about 20 mM.

In an embodiment, paracetamol is present an amount of from about 0.4 mg/mL to about 900 mg/mL. In an embodiment, paracetamol is present at a concentration of about 30 mM. In an embodiment, paracetamol is present at a concentration of about 60 mM.

In an embodiment, dexamethasone is present in an amount of from about 0.004 mg/mL to about 5.75 mg/mL. In an embodiment, dexamethasone is present in an amount of from about 1 mg/mL to about 5 mg/mL.

In an embodiment the heparin is present in an amount of from about 1.2 U/mL to 1200 U/mL. In an embodiment, the heparin is present in an amount of from about 1.2 U/mL to about 267 U/mL. In certain embodiments, the heparin concentration is less than 267 U/mL heparin.

In an embodiment, the salicylic acid concentration is from about 780 mg/mL to about 16,000 mg/mL. In an embodiment, the salicylic acid concentration is from about 0.18 mg/mL to about 1600 mg/mL. In an embodiment, the salicylic acid concentration is about 10 mM. In an embodiment, salicylic acid is present at a concentration of about 20 mM.

In an embodiment, the meloxicam concentration is from about 0.015 mg/mL to about 5.0 mg/mL. In an embodiment, meloxicam is present at a concentration of about 0.025 mg/mL to about 2.0 mg/mL. In an embodiment, meloxicam is present at a concentration of about 0.025 mg/mL to about 0.50 mg/mL. In an embodiment meloxicam is present at a concentration of about 1.5 mg/mL to about 3.0 mg/mL.

In an embodiment, the bromfenac concentration is from about 0.1 mg/mL to about 7.0 mg/mL. In an embodiment, bromfenac is present at a concentration of about 0.2 mg/mL to about 3.0 mg/mL. In an embodiment, bromfenac is present at a concentration of about 0.17 mg/mL to about 1.0 mg/mL. In an embodiment, bromfenac is present at a concentration of about 0.5 mg/mL to about 3.0 mg/mL.

Surfactants disclosed for use in parenteral pharmaceutical compositions include polysorbates, such as polysorbate 20 (TWEEN® 20) and polysorbate 80 (Tween® 80), polyethylene glycols such as PEG 400, PEG 3000, TRITON™ X-100, polyethylene glycols such as polyoxyethylene (23) lauryl ether (CAS Number: 9002-92-0, sold under trade name BRIJ®), alkoxylated fatty acids, such as MYRJ™, polypropylene glycols, block copolymers such as poloxamer 188 (CAS Number 9003-11-6, sold under trade name PLURONIC® F-68) and poloxamer 407 (PLURONIC® F127), sorbitan alkyl esters (e.g., SPAN®), maltosides, polyethoxylated castor oil (e.g., KOLLIPHOR®, CREMO-PHOR®) and trehalose and derivatives thereof, such as trehalose laurate ester. In certain embodiments, the surfactant is selected from the group consisting of polyoxyethylene (23) lauryl ether, poloxamer 188 trehalose laurate ester, polysorbate 20 and polysorbate 80. In an embodiment, the surfactant is poloxamer 188. In an embodiment, the surfactant is polysorbate 20. In an embodiment, the surfactant is polysorbate 80. In certain embodiments, the concentration of surfactant ranges from about 0.003 to about 2% w/v, about 0.003 to about 0.3% w/v or about 0.01 to about 0.2% w/v. In certain embodiments, the concentration of surfactant ranges from about 0.003 to about 2% w/v, about 0.003 to about 0.3% w/v or about 0.01 to about 0.2% w/v. In certain embodiments wherein the surfactant is poloxamer 188, the concentration of poloxamer 188 ranges from about 0.06 to about 0.12 w/v. In certain embodiments, the concentration of polysorbate 20 is about 0.06% w/v. In certain embodiments, poloxamer 188 is about 0.06% w/v. In other embodiments, the concentration of polysorbate 20 is about 0.09% w/v. In other embodiments, the concentration of polysorbate 20 is about 0.12% w/v. In other embodiments, the concentration of poloxamer 188 is about 0.12% w/v.

Use of CSII at a single site for 2 to 3 days is associated with wound formation from application of the infusion set and associated tissue remodeling, a defining factor in the efficacy of parenteral drug delivery systems and can vary from patient-to-patient. Wound formation and stimulation of fibrous encapsulation structures follows a complex series of inter-related biochemical pathways, which likely have genome-derived variations.

Beyond the wound and foreign body responses, additional considerations relate to patient sensitivity towards drugs like insulin and the excipients their formulations contain. There is a need for an insulin composition to facilitate use of CSII at a single site for more than 3 days for patients.

Dexamethasone is a corticosteroid, anti-inflammatory, and immunosuppressive. Glucocorticoids and the glucocorticoid receptor reside at the apex of a regulatory network that blocks inflammatory and immune pathways. The anti-inflammatory effects of glucocorticoids are largely due to a reduction in the synthesis and/or release of a variety of inflammatory mediators, including the prostaglandins that are also inhibited by non-steroidal anti-inflammatory drugs ("NSAIDS"). Glucocorticoids are shown to inhibit certain aspects of leukocyte function, which is associated with their immunosuppressant effect. Glucocorticoids inhibit phagocytosis among macrophages and reduce the number and activity of specific subsets of T lymphocytes. Compared to NSAIDS, glucocorticoids exhibit superior anti-inflammatory efficacy. Due to their somewhat delayed action, their effect on an initial catheter provisional matrix material may show differences compared to those medicines effecting hematostasis. Other glucocorticoid agents, such as betamethasone, are contemplated for use in an insulin composition of this invention. Other NSAIDS contemplated for use in an insulin composition of this invention include ibuprofen (about 12.8 mg/mL to about 1600 mg/mL), indomethacin (about 0.06 mg/mL to about 70 mg/mL), and salsalate (about 12 mg/mL to about 6000 mg/mL).

Heparin is an inhibitor of thrombin, binding to the enzyme inhibitor antithrombin III ("AT"), causing a conformational change that is associated with its activation. The activated AT is believed to inactivate thrombin, factor Xa, and other proteases reducing blood coagulation. The anticoagulation effects of heparin administration may reduce inflammatory signaling from the wound site. It is envisioned that heparin may interact with other inflammatory cytokines and proteins, further reducing the site fibrous matrix. Other agents envisioned herein that similarly inhibit the blood clotting cascade and may be useful in an insulin composition as claimed herein include abciximab (about 0.07 mg/mL to about 200 mg/mL), aggrastat (about 0.01 mg/mL to about 33.6 mg/mL), argatroban (about 0.77 mg/mL to about 768 mg/mL), eptifibitide (about 0.5 mg/mL to about 428 mg/mL), desirudin (about 0.12 mg/mL to about 120 mg/mL), dipyridamole (about 1.2 mg/mL to about 800 mg/mL), lepirudin (about 1.1 mg/mL to about 1120 mg/mL), and nafamostat (about 0.01 mg/mL to about 5.4 mg/mL).

As used herein "preservative" is selected from m-cresol, phenol, and mixtures thereof. In a preferred embodiment, the preservative is m-cresol. In certain embodiments, the concentration of m-cresol is from about 2.5 to about 3.8 mg/mL. In certain embodiments, the concentration of m-cresol is about 3.15 mg/mL. In certain embodiments, the phenol concentration is about 8.5 mg/mL. In certain embodiments, the preservative is a mixture of phenol and m-cresol. In certain embodiments, the preservative is a mixture of phenol at a concentration of about 1.5 mg/mL and m-cresol at a concentration of about 1.72 mg/mL.

As noted above, the present invention also provides an article of manufacture comprising a pharmaceutical composition. In certain embodiments, the article of manufacture is a multi-use vial. In other embodiments, the article of manufacture is a multi-use pre-filled cartridge. In other embodiments, the article of manufacture is a pump device for continuous subcutaneous insulin infusion therapy. In other embodiments, the article of manufacture is a container closure system for use in a pump device for continuous subcutaneous insulin infusion therapy In certain embodiments, the insulin concentration is from about 40 U/mL to about 1000 U/mL. In certain embodiments the insulin concentration is from about 100 U/mL to about 1000 U/mL.

In certain embodiments, the composition is stable to allow for use in a pump device for continuous subcutaneous insulin infusion therapy for up to 7 days. In certain embodiments, the composition is stable to allow for use in a pump device for CSII for up to 21 days.

The present invention is delivered locally to the site of CSII. As illustrated by the Examples, the formulation is placed in the insulin pump cartridge comprises insulin, a preservative, and the agent, However, the present invention envisions delivery of the agent locally to the infusion site. For example the agent may be provided by direct dissolution within the fluid path itself. Accordingly, any method that will deliver the agent in sufficient quantities and with a sufficient elution profile are envisioned. For example, the agents shown below illustrate this drug delivery profile:

| Drug | Concentration in Solution | Amount Delivered per day | Amount Delivered per week |
| --- | --- | --- | --- |
| Meloxicam | 0.015-0.050 mg/mL | 0.010-0.027 mg | 0.091-0.182 mg |
| Bromfenac sodium | 0.187-0.746 mg/mL | 0.101-0.403 mg | 0.707-2.820 mg |

-continued

| Drug | Concentration in Solution | Amount Delivered per day | Amount Delivered per week |
|---|---|---|---|
| Dexamethasone | 3.6 mg/mL | 6 mg | 42 mg |
| Salicylic Acid | 0.02 mmol/mL | 10.8 mmol | 75.6 mmol |

The abbreviations used herein are defined according to *Aldrichimica Acta*, Vol. 17, No. 1, 1984. Other abbreviations as used herein are defined as follows: "CSII" means continuous subcutaneous insulin infusion, "HPLC" refers to high performance liquid chromatography, "PBS" means phosphate-buffered saline, "HMWP" means high molecular weight polymer.

EXAMPLES

Example 1

Acetylsalicylic Acid and Acetaminophen

Preparation of Formulation Stocks:

Acetylsalicylic acid stock (30 mM) is prepared by adding 74.9 mg of solid to 13.9 mL of water. The acetylsalicylic acid stock solution is solubilized by the addition of a small aliquot (<50 uL) of 5 M NaOH to increase the pH to 12.5. Paracetamol stock (90 mM) is prepared by adding 101.7 mg of solid paracetamol to 7.5 mL of water (pH=5.3). The phosphate buffer stock (700 mM) is prepared by adding 1.5 g of $Na_2HPO_4$-$7H_2O$ to 8.1 mL of water (pH 9.0). The m-cresol stock solution (226.6 mM) is prepared by adding 49 mg of m-cresol to 2 mL of PBS. The zinc stock (30 mM) is prepared by adding 50.2 mg of zinc oxide (ZnO) to 20.6 mL of 75 mM HCl.

Insulin Co-Formulation Preparation:

Insulin lispro control formulation (750 uL) is prepared with a final concentration of 0.6 mM insulin lispro (3.5 mg/mL; 137.7 uL of 3267 uM $Zn^{2+}$ free stock), 29.13 mM m-cresol (3.15 mg/mL; 96.4 uL stock), 7 mM $Na_2HPO_4$-$7H_2O$ (7.5 uL of stock, pH 9.0), and 0.3 mM ZnO (7.5 uL of stock; 3 mol $Zn^{2+}$/hexamer). The insulin lispro/acetylsalicylic acid formulations are prepared as the control formulation above with a supplementation of 10 mM or 20 mM acetylsalicylic acid as final concentrations (250 uL and 500 uL of stock, respectively). Additionally, insulin lispro/paracetamol formulations are prepared as the control formulation above with a supplementation of 30 mM or 60 mM paracetamol as final concentrations (250 uL and 500 uL of stock, respectively). Two separate formulations are prepared as described above with 20 mM acetylsalicylic acid or 90 mM paracetamol; however, the m-cresol is excluded from the formulation. All samples are adjusted with water to achieve the final concentrations. The pH is adjusted to 7.4+/−0.1 with dilute HCl and/or NaOH. All samples are filtered using 0.22 um syringe filter (Millex-GV; REF SLGV013SL). An aliquot of 300 uL of each formulation described above, as well as an aliquot of 300 uL of commercial Humalog®, are placed into separate 2-mL screwcap glass vials and incubated static at 37° C. The insulin lispro main peak loss and high molecular weight polymer (HMWP) growth over time are tracked using analytical reversed-phase HPLC for 24 days. The samples are visibly inspected for particulate or precipitation throughout study.

Analytical RP-HPLC Conditions:

Insulin lispro main peak loss and HMWP growth are tracked over time using HPLC. Mobile phase buffer A (100 mM sodium sulfate+10% acetonitrile, pH to 2.3) and mobile phase buffer B (80% acetonitrile in water) are filtered through 0.22 um filter. The gradient is presented in Table 1. The UV detector is set to 214 nm wavelength, column temperature to 40° C., flowrate to 1 mL/min, and injection volume to 5 uL of each formulation. Main peak and HMWP are reported as an area percent from main peak region at approximately 10 mins retention time and HMWP region between 17 and 29 mins. The data is collected and slope analysis of rate of change per day is performed using Y by X plots using commercial software.

TABLE 1

Analytical RP-HPLC assay for determination of insulin main peak loss and polymer formation.

| Time (min) | Buffer A (%) | Buffer B (%) |
|---|---|---|
| 0.00 | 76.8 | 23.2 |
| 3.00 | 74.5 | 25.5 |
| 15.00 | 74.5 | 25.5 |
| 21.00 | 72.4 | 27.6 |
| 26.00 | 51.8 | 48.2 |
| 27.00 | 51.8 | 48.2 |
| 27.10 | 76.8 | 23.2 |
| 35.00 | 76.8 | 23.2 |

TABLE 2

Tabulated rates of change (%/day) for main peak loss and HMWP growth over time as determined by analytical RP-HPLC.

| Sample | Change in Main Peak (%/Day) | Change in HMWP (%/Day) |
|---|---|---|
| 10 mM Aspirin | −0.12 +/− 0.05 | 0.03 +/− 0.01 |
| 20 mM Aspirin | −0.17 +/− 0.11 | 0.09 +/− 0.07 |
| 20 mM Acetylsalicylic acid/No m-cresol | −1.47 +/− 0.26 | 0.84 +/− 0.17 |
| 30 mM Paracetamol | −0.33 +/− 0.22 | 0.14 +/− 0.03 |
| 60 mM Paracetamol | −0.37 +/− 0.01 | 0.27 +/− 0.05 |
| 60 mM Paracetamol/No m-cresol | −0.94 +/− 0.03 | 0.50 +/− 0.02 |
| Insulin lispro control | −0.16 +/− 0.05 | 0.04 +/− 0.003 |
| Commercial Humalog | −0.18 +/− 0.04 | 0.04 +/− 0.01 |

The tabulated data (Table 2) summarizes the rates of change (0%/day) in main peak and HMWP growth for insulin lispro co-formulated with either acetylsalicylic acid or paracetamol, in the absence and presence of m-cresol. For comparison, commercial Humalog® and laboratory prepared insulin lispro control, based on the Humalog® formulation, are presented as controls. The inclusion of acetylsalicylic acid or paracetamol has minimal impact on insulin lispro stability. The absence of m-cresol results in a higher rate of insulin main peak loss and polymer formation compared to m-cresol containing formulations.

Example 2

Heparin

Insulin with heparin formulations are prepared by adding 0.3 mL of heparin sodium (10,000 U/mL in water) and 0.58 mL of 0.9% sodium chloride to 10 mL of U110 insulin lispro to provide a final formulation comprising 276 U/mL heparin sodium, 101 U/mL insulin lispro, 16.22 mg/mL glycerin, 3.19 mg/mL m-cresol, 1.91 mg/mL sodium phosphate dibasic heptahydrate, 0.46 mg/mL sodium chloride, and 0.02 mg/mL $Zn^{2+}$. The insulin/heparin solution is transferred to pump cartridges for use in the pre-clinical in vivo model.

Pre-Clinical In Vivo Model:

A preclinical model using non-diabetic, castrated male Yucatan mini pigs in non-terminal, randomized, cross-over fashion is useful for mimicking the behavior of insulin pharmacokinetics and glucose pharmacodynamics in human subjects over the course of continuous infusion at a single infusion site for up to 10 days. In this model, one infusion set is placed on the abdomen of each animal, and each site receives the same volume of insulin placebo (formulations identical to U100 Humalog® but containing no active pharmaceutical ingredient) for 3× daily bolus infusion of 0.1 mL, and continuous basal infusion of 0.01 mL/h. Test groups with non-insulin medicaments receive placebo with the medicament added at the desired concentration. On days 0, 3, 5, 7, and 10 following infusion set placement, after an overnight fast, each animal is given an infusion bolus of U100 Humalog (with or without a non-insulin medicament) in accordance with their body weight (0.15 U/kg). Glucose and insulin concentrations are then assessed via serial blood samples collected from each animal at the following time points relative to the time of insulin bolus delivery: −30, −20, 0, (deliver insulin bolus), 15, 30, 45, 60, 75, 90, 120, 150, 180, 240, 300, and 360 min. At conclusion of blood sampling on day 10, infusion sets are carefully removed and assessed for catheter damage. The site of infusion is also assessed for signed of infection, irritation, erythema, and edema. This model can demonstrate significant reductions in plasma insulin concentrations and consequent glucose lowering over time indicative of the loss of infusion site efficacy. The pre-clinical model is used to show the effects of compositions claimed herein.

The data in Table 3 represents the insulin pharmacokinetic data for U100 Humalog and the insulin/heparin co-formulation, respectively, and over the course of 10 days of continuous infusion at a single infusion site. The diminishing concentration of serum insulin over time for the Control Group of Table 3 is typical for CSII, while the maintenance of insulin pharmacokinetics without any loss in signal for 7 consecutive days for the insulin/heparin co-formulation Test Group in Table 3 supports the desired result.

TABLE 3

Maximum changes in plasma glucose concentration after dosing with 0.15 U/kg of U100 insulin lispro or 0.15 U/kg of U100 insulin lispro spiked with 267 U/mL heparin sodium, on days 0, 3, 5, 7, and 10 of continuous infusion at a single infusion site. Variation is standard error of the mean. P-values derived via a 2-sample T-test.

| Days of Continuous Infusion | Maximum Change in Plasma Glucose (Mean ± SEM) | | P-value ($\alpha$ = 0.05) |
|---|---|---|---|
| | Control Group (N = 6) | Heparin-Treated (N = 7) | |
| 0 | −71.8 ± 5.2 | −66.9 ± 2.6 | 0.416 |
| 3 | −57.0 ± 6.0 | −65.1 ± 2.7 | 0.261 |
| 5 | −42.2 ± 8.0 | −62.0 ± 2.8 | 0.057 |
| 7 | −36.2 ± 10.3 | −62.9 ± 5.3 | 0.055 |
| 10 | −39.1 ± 10.4 | −22.3 ± 8.7 | 0.247 |

The effect on insulin efficacy is further demonstrated by evaluating the maximum serum insulin concentrations over time. This study showed that the glucose lowering effect of an insulin bolus is sustained for 7 days in heparin-treated animals, but steadily declines from day 0 in animals not treated with heparin. N=6 for each group.

Example 3

Dexamethasone

This study can be used to evaluate the beneficial effect of local delivery of dexamethasone during SCII. In this experiment, dexamethasone is not co-formulated with insulin; rather, the 0.25 mg/h infusion is achieved using a commercially available solution of 10 mg/mL dexamethasone delivered using an infusion pump programmed for a basal delivery of 25 uL/h. On days 0, 3, 5, 7, and 10 following infusion set placement, the animals are fasted followed by dosing with 0.15 U/kg insulin lispro using an infusion pump. During the time between insulin doses, the animals receive 25 uL/h continuous infusion of either 10 mg/mL dexamethasone or insulin placebo.

Results using the methods set forth support that local delivery of dexamethosone via co-formulation with insulin is a preferred route of administration to achieve the desired result. Results from the study support that the concentration of 0.25 mg/h (6 mg/d) is effective in improving infusion site viability for 5 days.

Dexamethasone insulin formulations are prepared substantially as follows: 1.1 mL of a 100 mg/mL dexamethasone solution in sodium phosphate buffer is added to 10 mL U110 insulin lispro. The formulation is prepared using standard techniques to provide a formulation comprising 10 mg/mL dexamethasone, 99 U/mL insulin lispro, 15.84 mg/mL glycerin, 3.12 mg/mL m-cresol, 2.07 mg/mL sodium phosphate, and 0.02 mg/mL $Zn^2$.

Results shown in Table 4 indicate that dexamethasone can improve infusion site viability for up to 5 days, whereas orally delivered dexamethasone has no effect.

TABLE 4

Baseline-adjusted areas under the curve for plasma glucose over the 6 hours following an insulin bolus of 0.15 U/kg of U100 insulin lispro, on days 0, 3, 5, 7, and 10 of continuous infusion of 0.25 mg/h dexamethasone (Subcutaneous Dexamethasone), 25 uL/h insulin placebo (Control Group), and 25 uL/h insulin placebo + twice daily oral administration of 3 mg dexamethasone (Oral Dexamethasone). Variation is standard error of the mean. P-values derived via a 2-sample T-test between the Subcutaneous Dexamethasone and Control Group data sets.

| | Plasma Glucose | | | |
| Days of Continuous Infusion | Control Group (N = 5) | Subcutaneous Dexamethasone (N = 5)* | Oral Dexamethasone (N = 5) | * P-value vs. Control ($\alpha$ = 0.05) |
| --- | --- | --- | --- | --- |
| 0 | −15110 ± 2482 | −16700 ± 2027 | −14218 ± 754 | 0.635 |
| 3 | −7015 ± 2418 | −12591 ± 873 | −5265 ± 2130 | 0.082 |
| 5 | −8266 ± 1422 | −12297 ± 755 | −8109 ± 987 | 0.046 |
| 7 | −5517 ± 1340 | −7149 ± 1555 | −7750 ± 1491 | 0.453 |
| 10 | −4440 ± 1242 | −4893 ± 775 | −4266 ± 1551 | 0.767 |

Example 4

Meloxicam and Bromfenac Sodium

Preparation of Formulation Stocks:

Humalog U200 stock solution is prepared by dissolving 7.55 g of insulin lispro powder in approximately 788 g of mixture containing 3.15 g of m-cresol, 16 g of glycerin in water, supplemented with 1.96 mL of 12.44 mg/mL of zinc oxide stock solution. After adding insulin lispro powder, the pH of the solution is reduced to pH 3.0+/−0.2 by adding suitable amount of 10% w/w HCl and stirring until complete dissolution is observed or up to a maximum of 2 hours. Following insulin lispro dissolution, the pH of the solution is increased to pH 7.6+/−0.1 by adding suitable amount of 10% w/w NaOH, allowing the mixture to re-dissolve the solids for 30 minutes and then adjusting the pH down to pH 7.3+/−0.1. Then, 90 mL of Tris base prepared at 55.55 mM and pH 7.2-pH 7.4 in water is added to this solution After this, the solution pH is adjusted down to pH 7.25+/−0.5 by adding suitable volume of 10% w/w HCl. The solution is supplemented with additional water until its weight equals 915 g. The final solution is mixed for another 5 minutes and then filtered through a 0.22 um PVDF filter into a clean container.

Meloxicam stock (3.0 mg/mL) is prepared by adding 179.8 mg of solid first to 20 mL of water, then increasing the pH to above pH 12.0 using 10% w/w NaOH, followed by addition of more water until 59.8 mL of total water volume has been added. This stock solution is mixed for at least 30 minutes or until complete dissolution is observed.

Humalog U200-Meloxicam Co-Formulation Preparation:

The Humalog U220 stock solution is taken in clean glass beakers with a stir bars. Suitable volume of the meloxicam (3 mg/mL) stock solution is added along with suitable volume of water to equal 0.01, 0.05, 0.18, or 0.27 mg/mL meloxicam and mixed well. The pH of the solution is adjusted at pH 7.25+/−0.05 by adding suitable volume of 10% w/w HCl. Each solution is filtered through 0.22 um PVDF filters and then filled into clean glass vials. The vials are kept at 30° C. for 36 days.

Humalog U200-Bromfenac Sodium Co-Formulation Preparation:

The Humalog U220 stock solution is diluted with water to equal to U200/mL insulin lispro concentration. Suitable quantity of Bromfenac Sodium powder is weighed out in separate clean glass beakers with a target volume of 200-220 mL of solution containing 0.075, 0.187 and 0.746 mg/mL bromfenac sodium respectively. Based on the weighed quantity, the appropriate volume of Humalog U200 prepared earlier is added and mixed for 5 minutes to fully dissolve the bromfenac sodium. The resulting solution filtered through 0.22 um PVDF filters and then filled into clean glass vials. The vials are kept at 30° C. for 36 days.

Analytical SEC Conditions for Humalog U200-Meloxicam Coformulation Samples

The mobile phase is prepared by mixing a 1.0 mg/mL stock solution of L-arginine with acetonitrile and glacial acetic acid in the ratio 65:20:15 respectively. The mobile phase is flowed at 0.5 mL/min through a size-exclusion HPLC column maintained at ambient temperature (WAT201549, 30 cm×7.8 mm, Waters). 50 uL of each coformulation sample is injected and monitored for a run time of 40 minutes at 276 nm using a UV-Visible detector. Main peak and high molecular weight polymer (HMWP) are reported as an area percent from main peak region at approximately 18 mins retention time and HMWP region between 10 and 17 mins. The data is collected at different points during the 36-day incubation period at 30° C. Using slope analysis, the rate of change of HMWP per day is performed using Y by X plots using commercial software.

Analytical SEC Conditions for Humalog U200—Bromfenac Sodium Coformulation Samples:

The mobile phase is prepared by mixing acetonitrile and water in 1:1 volume ratio and further mixing trifluoroacetic acid (TFA) at 0.1% volume ratio in the solution. The mobile phase is flowed at 1.2 mL/min through a size-exclusion HPLC column maintained at ambient temperature (233080-7830, 300 mm×7.8 mm, Sepax Technologies). 25 uL of each coformulation sample is injected and monitored at 276 nm using a UV-Visible detector for 15 minutes. Main peak and high molecular weight polymer (HMWP) are reported as an area percent from main peak region at approximately 5.6 mins retention time and HMWP region between 4 and 5.2 mins. The data is collected at different points during the 36-day incubation period at 30° C. Using slope analysis, the rate of change of HMWP per day is performed using Y by X plots using commercial software.

TABLE 3

Tabulated rates of change (%/day) for main peak loss and HMWP growth over time as determined by analytical RP-HPLC.

| Sample | Change in HMWP (%/Day) |
|---|---|
| Humalog U200 + 0.01 mg/mL meloxicam | 0.0091 |
| Humalog U200 + 0.05 mg/mL meloxicam | 0.0091 |
| Humalog U200 + 0.18 mg/mL meloxicam | 0.0082 |
| Humalog U200 + 0.27 mg/mL meloxicam | 0.0079 |
| Humalog U200 control | 0.0079 |
| Humalog U200 + 0.075 mg/mL bromfenac sodium | 0.0079 |
| Humalog U200 + 0.187 mg/mL bromfenac sodium | 0.0089 |
| Humalog U200 + 0.746 mg/mL bromfenac sodium | 0.00122 |

Data Analysis Methodology

There are four parameters that we most often use to evaluate the effects of an intervention on glucose pharmacodynamics: the baseline subtracted area under the glucose PD curve (AUC); $C_{min}$, or the maximum change from baseline that the insulin dose effects; $T_{min}$, or the time it takes to reach $C_{min}$ after the insulin dose is administered; and the "Early 50% $T_{min}$", or the time it takes to first reach a glucose concentration that is 50% the magnitude of $C_{min}$. Table 4 below represents typical PD data for a non-diabetic swine that has been fasted and dosed with 0.15 U/kg of U100 insulin lispro, delivered via an infusion set that has been in place for up to 10 days. Between insulin doses, the infusion set is connected to an insulin pump programmed to deliver insulin placebo at a 10 uL/h basal rate and 100 ul boluses delivered three times daily. SEM=standard error of the mean.

TABLE 4

Typical PD data for a non-diabetic swine

| | Days of CSI | N | Mean | SEM | Std Dev |
|---|---|---|---|---|---|
| $C_{min}$ | 0 | 34 | −61.32 | 1.74 | 10.15 |
| (Δ mg/dL) | 3 | 33 | −57.31 | 1.88 | 10.79 |
| | 5 | 30 | −58.16 | 2.37 | 13 |
| | 7 | 29 | −45.12 | 3.64 | 19.63 |
| | 10 | 26 | −30.44 | 3.18 | 16.23 |
| $T_{min}$ | 0 | 34 | 69.26 | 7.33 | 42.75 |
| (min) | 3 | 33 | 52.73 | 6.69 | 38.45 |
| | 5 | 30 | 40 | 3.9 | 21.33 |
| | 7 | 29 | 69.3 | 17 | 91.5 |
| | 10 | 26 | 96.9 | 20 | 101.9 |
| AUC | 0 | 34 | −13196 | 602 | 3511 |
| (min*mg/dL) | 3 | 33 | −9702 | 529 | 3039 |
| | 5 | 30 | −8277 | 620 | 3394 |
| | 7 | 29 | −6115 | 566 | 3049 |
| | 10 | 26 | −4213 | 509 | 2595 |

As is demonstrated above by the shift in PD parameters from day 0 to day 3, starting at around day 2 of continuous subcutaneous insulin infusion (CSII), insulin uptake becomes faster, and depending on pump speed, some loss in AUC may also be observed. This phenomenon has been well characterized by researchers (sometimes referred to as the "Tamborlane effect") and is well-tolerated by patients. Thus, a solution to enabling extended infusion site efficacy should strive to achieve some level of equivalence to the glycemic control patients experience on day 3 of CSII. In the interventions set forth herein, we have thus evaluated the resulting PD performance against the standard of care (a rapid-acting insulin such as Humalog®) after 3 days of CSII. Data from swine studies set forth in Tables 5, 6, and 7 show the efficacy of three formulations at days 0, 3, 5, 7, and 10 normalized against U100 Humalog values on day 3.

TABLE 5

Glucose Area Under the Curve v. Standard of Care Day 3

| Formulation | Metric | Glucose AUC % Difference vs U100 Humalog AUC on Day 3 (mean of −10608 min * mg/dL, n = 53) | | | | |
|---|---|---|---|---|---|---|
| | | Day 0 | Day 3 | Day 5 | Day 7 | Day 10 |
| U100 Humalog + 0.025 mg/mL Meloxicam | n | 19 | 19 | 19 | 19 | 18 |
| | Mean (min * mg/dL) | −12798 | −11005 | −10145 | −6650 | −5287 |
| | % Difference | 21% | 4% | −4% | −37% | −50% |
| | p-value | 0.036 | 0.704 | 0.658 | 0.000 | 0.000 |
| U100 Humalog + 0.050 mg/mL Meloxicam | n | 14 | 14 | 14 | 14 | 13 |
| | Mean (min * mg/dL) | −14675 | −8205 | −7496 | −8219 | −5950 |
| | % Difference | 38% | −23% | −29% | −23% | −44% |
| | p-value | 0.001 | 0.049 | 0.011 | 0.050 | 0.000 |
| U100 Humalog + 0.70 mg/mL Bromfenac Sodium | n | 18 | 19 | 19 | 19 | 19 |
| | Mean (min * mg/dL) | −16184 | −12471 | −11005 | −8360 | −7504 |
| | % Difference | 53% | 18% | 4% | −21% | −29% |
| | p-value | 0.000 | 0.099 | 0.725 | 0.047 | 0.006 |

TABLE 6

Glucose Cmin % v. Standard of Care Day 3

| Formulation | Metric | Glucose Cmin % Difference vs U100 Humalog Cmin on Day 3 (mean of −59 mg/dL, n = 53) | | | | |
|---|---|---|---|---|---|---|
| | | Day 0 | Day 3 | Day 5 | Day 7 | Day 10 |
| U100 Humalog + 0.025 mg/mL | N | 19 | 19 | 19 | 19 | 18 |
| | Mean (Δ | −56 | −60 | −60 | −54 | −33 |

TABLE 6-continued

Glucose Cmin % v. Standard of Care Day 3

| | | Glucose Cmin % Difference vs U100 Humalog Cmin on Day 3 (mean of −59 mg/dL, n = 53) | | | | |
|---|---|---|---|---|---|---|
| Formulation | Metric | Day 0 | Day 3 | Day 5 | Day 7 | Day 10 |
| Meloxicam | mg/dL) | | | | | |
| | % Difference | −5% | 1% | 2% | −8% | −44% |
| | p-value | 0.468 | 0.856 | 0.817 | 0.248 | 0.000 |
| U100 Humalog + 0.050 mg/mL Meloxicam | n | 14 | 14 | 14 | 14 | 13 |
| | Mean (Δ mg/dL) | −61 | −55 | −57 | −57 | −45 |
| | % Difference | 2% | −8% | −4% | −4% | −24% |
| | p-value | 0.773 | 0.346 | 0.667 | 0.656 | 0.005 |
| U100 Humalog + 0.70 mg/mL Bromfenac Sodium | n | 18 | 19 | 19 | 19 | 19 |
| | Mean (Δ mg/dL) | −62 | −60 | −58 | −52 | −46 |
| | % Difference | 5% | 1% | −3% | −13% | −22% |
| | p-value | 0.524 | 0.935 | 0.735 | 0.085 | 0.004 |

TABLE 7

Glucose Tmin % v. Standard of Care Day 3

| | | Glucose Tmin % Difference vs U100 Humalog Tmin on Day 3 (mean of 41 min, n = 53) | | | | |
|---|---|---|---|---|---|---|
| Formulation | Metric | Day 0 | Day 3 | Day 5 | Day 7 | Day 10 |
| U100 Humalog + 0.025 mg/mL Meloxicam | n | 19 | 19 | 19 | 19 | 18 |
| | Mean (min) | 56 | 29 | 33 | 68 | 144 |
| | % Difference | 37% | −29% | −19% | 68% | 253% |
| | p-value | 0.338 | 0.452 | 0.616 | 0.078 | 0.000 |
| U100 Humalog + 0.050 mg/mL Meloxicam | n | 14 | 14 | 14 | 14 | 13 |
| | Mean (min) | 72 | 53 | 55 | 50 | 52 |
| | % Difference | 76% | 29% | 34% | 24% | 27% |
| | p-value | 0.084 | 0.513 | 0.439 | 0.592 | 0.555 |
| U100 Humalog + 0.70 mg/mL Bromfenac Sodium | n | 18 | 19 | 19 | 19 | 19 |
| | Mean (min) | 64 | 43 | 59 | 47 | 60 |
| | % Difference | 56% | 6% | 45% | 16% | 47% |
| | p-value | 0.177 | 0.879 | 0.270 | 0.696 | 0.250 |

We claim:

1. A method of treating diabetes comprising administering to a human in need thereof an effective dose of a pharmaceutical composition comprising:

(a) rapid acting insulin or ultra-rapid acting insulin;

(b) m-cresol; and (c) meloxicam, wherein the insulin concentration is from about 100 U/mL to about 500 U/mL, the concentration of m-cresol is from about 2.5 mg/mL to about 3.8 mg/mL, and the concentration of meloxicam is from about 0.015 mg/ml to about 5.0 mg/mL.

*   *   *   *   *